(12) United States Patent
Cheetham

(10) Patent No.: US 8,714,354 B2
(45) Date of Patent: May 6, 2014

(54) LIQUID CONTAINER

(75) Inventor: Joshua James Cheetham, Bensenville, IL (US)

(73) Assignee: SDI North America Inc., Bensenville, IL (US)

(*) Notice: Subject to any disclaimer, the term of this patent is extended or adjusted under 35 U.S.C. 154(b) by 0 days.

(21) Appl. No.: 12/897,562

(22) Filed: Oct. 4, 2010

(65) Prior Publication Data

US 2011/0233214 A1    Sep. 29, 2011

(30) Foreign Application Priority Data

Mar. 25, 2010  (AU) .............................. 2010901260

(51) Int. Cl.
  *B65D 1/36*    (2006.01)
(52) U.S. Cl.
  USPC ......................................................... 206/368
(58) Field of Classification Search
  CPC ..... A61C 19/005; A61C 5/068; B65D 51/002
  USPC ................ 206/368, 369, 63.5, 219, 221, 222;
      220/608, 265, 716, 254.1, 258.1;
      215/224, 297, 307
  See application file for complete search history.

(56) References Cited

U.S. PATENT DOCUMENTS

| | | | | |
|---|---|---|---|---|
| 1,394,391 A * | 10/1921 | Woolsey | ...................... | 206/63.5 |
| 3,881,627 A * | 5/1975 | Davolt | ......................... | 215/329 |
| 4,362,242 A * | 12/1982 | Cheetham | ..................... | 206/219 |
| 4,508,235 A * | 4/1985 | Steele et al. | ................... | 215/307 |
| 6,000,535 A * | 12/1999 | Berk et al. | ..................... | 206/63.5 |
| 6,446,827 B1 * | 9/2002 | Akins | ......................... | 220/570 |
| 7,331,450 B2 * | 2/2008 | Discko, Jr. | ................... | 206/63.5 |
| 2002/0119222 A1 * | 8/2002 | Searle et al. | ................... | 426/115 |
| 2002/0124773 A1 * | 9/2002 | Diesso | ............................ | 106/35 |
| 2004/0020796 A1 * | 2/2004 | Cheetham et al. | ........... | 206/63.5 |
| 2004/0157205 A1 * | 8/2004 | Etheredge et al. | ............. | 435/1.1 |
| 2009/0250359 A1 * | 10/2009 | Chae et al. | .................... | 206/219 |

OTHER PUBLICATIONS

English language abstract of KR20030068109 (A), publication date Aug. 19, 2003.
International Search Report by ISA/AU of related application PCT/AU2010/001296, mailed Oct. 28, 2010.

* cited by examiner

*Primary Examiner* — Steven A. Reynolds
*Assistant Examiner* — King M Chu
(74) *Attorney, Agent, or Firm* — William H. Holt

(57) ABSTRACT

A liquid container (10) has an outer wall (12) to which is mounted a liquid material receptacle (18). The liquid material receptacle has an open end (20) and a closed end (24). The open end (20) of the liquid material receptacle (18) is sealed by a membrane (34). Further, the liquid material receptacle (18) tapers inwardly from the open end (20) to the closed end (24).

9 Claims, 3 Drawing Sheets

LIQUID CONTAINER

FIELD OF THE INVENTION

The present invention relates to a liquid container.

SUMMARY OF THE INVENTION

In accordance with one aspect of the present invention there is provided a liquid container comprising an outer wall having an upper end and a lower end, a liquid material receptacle mounted adjacent to the upper end of the outer wall internally of the outer wall, the liquid material receptacle having an open end adjacent the upper end of the outer wall, and a closed end remote from the upper end of the outer wall, wherein the liquid material receptacle is sealed by a membrane which is arranged to be broken by an applicator.

DESCRIPTION OF THE DRAWINGS

The present invention will now be described, by way of example, with reference to the accompanying drawings, in which.

DETAILED DESCRIPTION OF THE INVENTION

Figure 1:
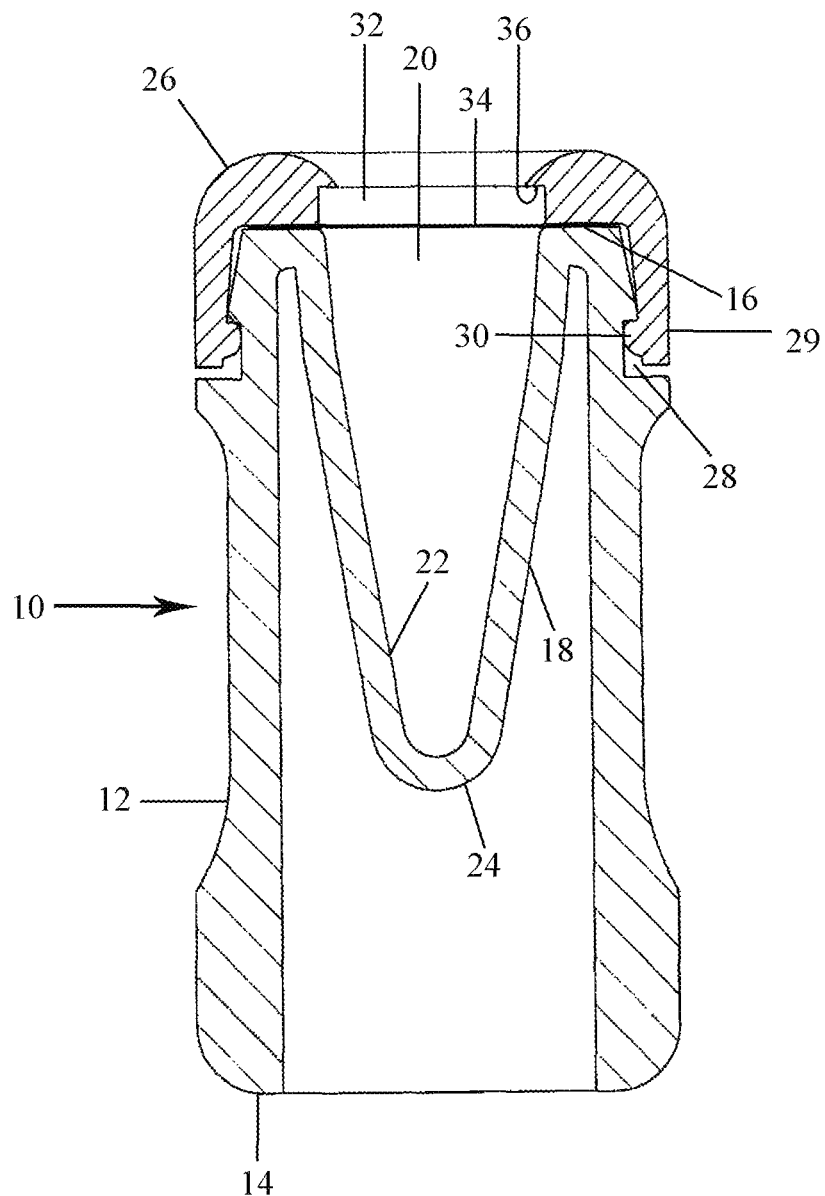
FIG. 1 is a side view of the container of the present invention.
Figure 2:
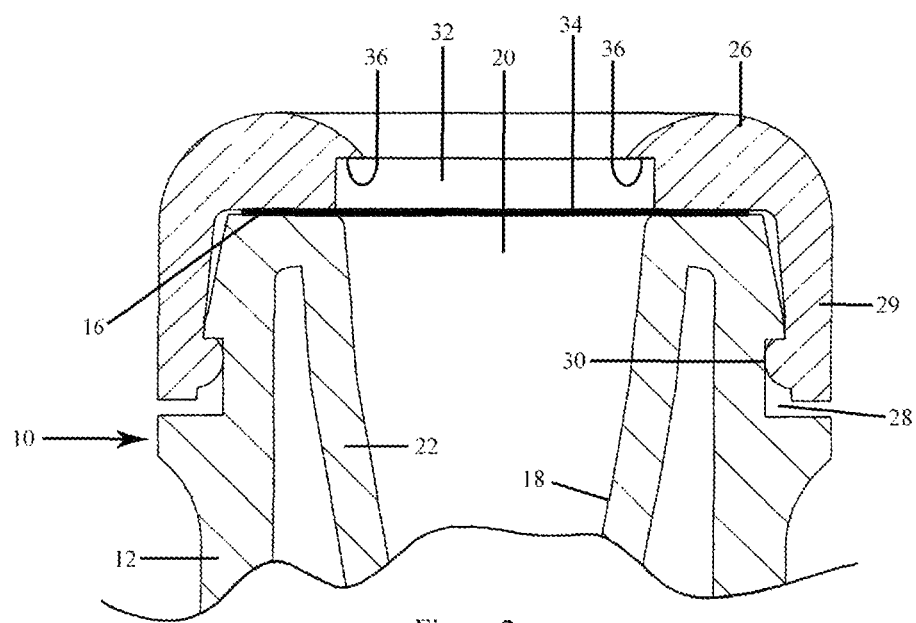
FIG. 2 is a partial view of the container of FIG. 1 showing an upper part of the container to an enlarged scale.

In the drawings there is shown a container 10 comprising an outer circumferential wall 12. The wall 12 has a lower end 14 which is substantially horizontal and which enables the container 10 to rest in stable manner on a flat surface.

The wall 12 also has an upper end 16. A liquid material receptacle 18 is mounted adjacent to the upper end 16 of the wall 12 internally of the wall 12. Further, the receptacle 18 depends from the upper end 16 as can best be seen in FIG. 1. As shown, the receptacle 18 has an open end 20 which is adjacent the upper end 16 and an endless inwardly facing side wall 22 which terminates in a closed end 24 which is remote from the upper end 16.

Further, the container 10 is provided with a cap 26 which is arranged to engage with the outer wall 12 adjacent the upper end 16 thereof.

Further, adjacent the upper end 16 of the wall 12 the container 10 is provided with a circumferential groove 28. Still further, the cap 26 is provided with a downwardly extending circumferential flange 29 which is provided with an internal lip 30. The lip 30 is arranged to engage with the groove 28.

Further, the cap 26 is apertured having a central aperture 32 which is surrounded by an inwardly facing lip 36.

Prior to use the container 10 is sealed by a membrane 34 which is preferably flexible. This membrane 34 may be a layer of foil. The membrane 34 extends across the open end 20 of the liquid material receptacle 18 between the cap 26 and the upper end 16 of the wall 12. The membrane 34 preferably has a layer of adhesive, usually on an underside thereof, as seen in FIG. 1, to ensure sealing engagement with the wall 12. The membrane 34 and the layer of adhesive may be heat sealed to the wall 12 or sealed by other means.

Referring to FIGS. 3a to 3d there is shown assembly of the container 10 and the use thereof.

Figure 3:
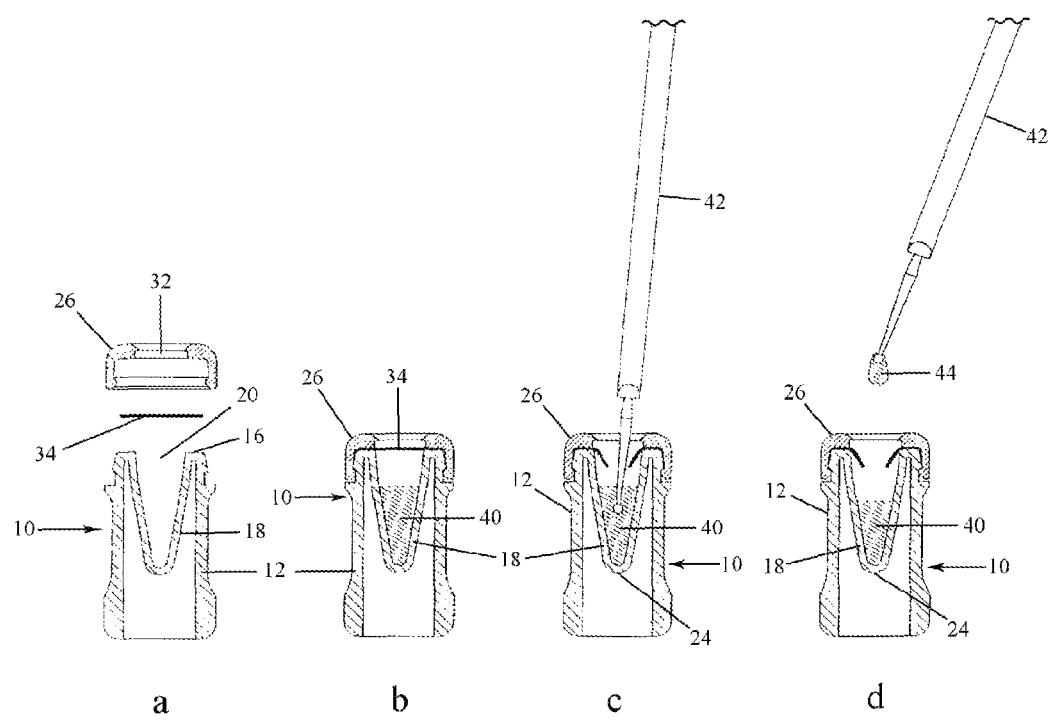
FIGS. 3a to 3d show assembly and use of the container of FIGS. 1 and 2.

In FIG. 3a the membrane 34 is being applied to the upper end 16 of the wall 12 followed by the cap 26.

In FIG. 3b the container 10 is shown fully assembled and containing a liquid material 40, typically a liquid dental adhesive, in the liquid material receptacle 18.

In FIG. 3c it can be seen that the membrane 34 has been broken by an applicator 42 which has been manually inserted through the aperture 32 into the liquid material 40.

In FIG. 3d there is shown the applicator 42 after withdrawal from the container 10 with a drop of liquid material 44 on a lower end of the applicator 42.

The lip 36 is arranged to wipe off excess liquid material from the applicator 42 after the step of FIG. 3d.

Preferably the membrane 34 has a thickness in the range from 0.001 mm to 0.2 mm, more preferably from 0.005 mm to 0.04 mm.

The wall 12 enables the container 10 to be held in one hand by a user whilst the other hand can be used for the applicator 42 which may be a brush such as an adhesive brush.

The container of the present invention is of general applicability but it is particularly envisaged for use with liquid dental materials such as a dental adhesive.

Modifications and variations as would be apparent to a skilled addressee are deemed to be within the scope of the present invention.

The invention claimed is:

1. A liquid container comprising an outer wall having an upper end and a lower end, a liquid material receptacle mounted to said outer wall internally thereof and adjacent to said upper end thereof, and a cap for closing said upper end, said liquid material receptacle having an open end adjacent said upper end of said outer wall and a closed end remote from said upper end of said outer wall, said liquid material receptacle tapering inwardly and downwardly from said open end thereof to adjacent said closed end, said outer wall adjacent said upper end thereof being provided with a circumferential groove, said cap engaging with said outer wall externally adjacent thereof to said upper end, said cap being provided with a downwardly extending circumferential flange having an internal lip which engages with said circumferential groove, said cap having an upper central aperture adjacent said open end of said liquid material receptacle and said liquid material receptacle being sealed by a membrane which extends across said central aperture of said cap and said open end of said liquid receptacle, said central aperture and said open end being of substantially the same size and said membrane being disposed between said upper end of the said wall and said cap.

2. A liquid container according to claim 1, wherein said lower end of said outer wall is substantially flat and enables said liquid container to rest in stable manner on a flat surface.

3. A liquid container according to claim 2, wherein said outer wall extends circumferentially around said liquid material receptacle.

4. A liquid container according to claim 1, wherein said outer wall extends circumferentially around said liquid material receptacle.

5. A liquid container according to claim 1, wherein said liquid material receptacle depends from said upper end of said outer wall.

6. A liquid container according to claim 1, wherein said apertured cap includes a central aperture surrounded by an internal lip arranged for wiping off excess liquid material from an applicator.

7. A liquid container according to claim 1, wherein said liquid material receptacle contains a liquid material.

8. A liquid container according to claim 1, wherein said membrane has a thickness in the range from 0.005 mm to 0.04 mm.

9. A liquid container according to claim 1 wherein said outer wall adjacent said upper end thereof is provided with a circumferential groove, said cap engages with said outer wall externally thereof adjacent said upper end, and wherein said cap is provided with a downwardly extending circumferential groove.

\* \* \* \* \*